ized Patent

United States Patent [19]
Bertelli et al.

[11] Patent Number: 5,182,321
[45] Date of Patent: Jan. 26, 1993

[54] PIPERAZINE CYANURATE AND POLYMER COMPOSITIONS COMPRISING IT

[75] Inventors: Guido Bertelli, Ferrara; Osvaldo Cicchetti, Milan; Paolo Goberti; Renato Locatelli, both of Ferrara, all of Italy

[73] Assignee: HIMONT Incorporated, Wilmington, Del.

[21] Appl. No.: 809,811

[22] Filed: Dec. 18, 1991

[30] Foreign Application Priority Data

Dec. 20, 1990 [IT] Italy ................... 22454 A/90

[51] Int. Cl.$^5$ ................... C08K 5/3492; C07D 403/02
[52] U.S. Cl. ................... 524/100; 524/416; 524/417; 544/219

[58] Field of Search ................ 544/219; 524/100, 416, 524/417

[56] References Cited

U.S. PATENT DOCUMENTS 4,180,496 12/1979 Yansgimoto et al. ................ 524/100

FOREIGN PATENT DOCUMENTS 79070 3/1977 Japan .

Primary Examiner—Kriellion S. Morgan

[57] ABSTRACT

Piperazine cyanurate with specified formula and its use in the preparation of self-extinguishing polymer compositions.

6 Claims, No Drawings

PIPERAZINE CYANURATE AND POLYMER COMPOSITIONS COMPRISING IT

The present invention relates to piperazine cyanurate having the formula

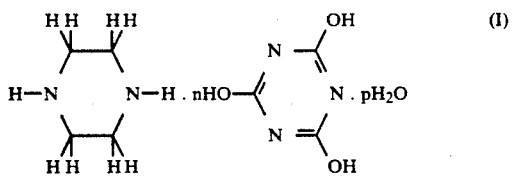

where n is from 1 to 2 and p from 0 to 3, self-extinguishing compositions based on thermoplastic polymers or polymers with elastomeric properties, in particular olefin polymers or copolymers, comprising the product of the reaction between cyanuric acid and piperazine, said product comprising or being constituted by one or more of the compounds of the formula (I).

Various solutions for reducing or eliminating polymer combustibility are known in the art. Some such solutions are based on the use of metal compounds, especially of antimony, bismuth or arsenic, in combination with partially halogenated and thermally unstable organic compounds, such as chlorinated paraffin waxes.

Other solutions are based on the use of substances capable of producing intumescence. The intumescent formulations generally consist of the polymer and at least three main additives: an acid compound or one capable of generating acid during combustion, the purpose of which is to activate the process of the formation of intumescence; a second additive containing nitrogen which acts as a foaming agent; and a third additive which contains carbon, which acts as a donor of carbon for the formation of an insulating cellular carbon layer (char) between polymer and flame.

Examples of intumescent fromulations of the above types are those reported by patents: U.S. Pat. No. 3,810,862 (Phillips Petroleum Co.) based on melamine, pentaerythrite and ammonium polyphosphate; U.S. Pat. No. 4,727,102 (Vamp S.r.l.) based on melamine cyanurate, a hydroxyalkyl derivative of isocyanuric acid and ammonium polyphosphate; and by published Patent Application No. WO 85/05626 (Plascoat U.K. Limited), based on various compounds of phosphorus and nitrogen, in particular a combination of melamine phosphate, pentaerythrite and ammonium polyphosphate.

In more recent formulations, in addition to the use of an organic or inorganic phosphorus compound, an organic compound containing nitrogen, generally an amino resin obtained by condensation of urea, melamine or dicyandiamide with formaldehyde has been used.

An example of a formulation with two additives is reported in U.S. Pat. No. 4,193,945 (Montedison S.p.A.) based on ammonium polyphosphate and particular nitrogen organic compounds containing the groups >C═O and/or >C═S and >NH inserted into a cyclic structure.

It is also possible to obtain self-extinguishing compositions using single-component additives, containing both nitrogen and phosphorus in the organic molecule, as described in U.S. Pat. No. 4,201,705 (Borg-Warner Corp.) and in U.S. Pat. No. 4,599,375 (Montedison S.p.A.).

However, it is known that the salts of pyrophosphoric acid (such as those described, for example, in U.S. Pat. No. 4,599,375) are hygroscopic and easily hydrolyzable; thus, when these are used as flame retardants for the preparation of self-extinguishing polymer compositions, their use, at least in certain applications, can cause migration to the surface (blooming) and make the products sticky.

In published European Patent Application No. 286,478 (Atochem), self-extinguishing compositions comprising salts formed by phosphorous acid and by amines, such as s-triazine, 1,2,4-triazole, benzimidazole, heptazine, pyrimidine, morpholine or piperazine are described.

These intumescent retardant systems allow the polymer containing them to form a carbon residue after a fire or the application of a flame. The retardant systems of this type present numerous advantages: absence of corrosion of the machinery in which the polymers are processed, lower emission of fumes with respect to the systems containing metal compounds and halogenated hydrocarbons, and above all the possibility of giving to the polymers satisfactory flame-resistant properties with a smaller quantity of total additive and thus without an excessive decline in the mechanical properties of the polymers.

It has now been found that polymer compositions endowed with improved flame-resistant properties can be obtained using the product of the reaction between cyanuric acid and piperazine.

Said product comprises or consists of one or more of the compounds represented by the following formula:

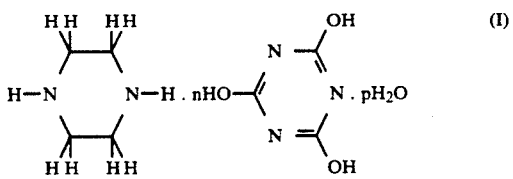

where n is from 1 to 2 and p from 0 to 3.

The formula (I) piperazine cyanurate constitutes a another embodiment of the present invention.

The compositions of the present invention preferably comprise:

a) from 90 to 50, preferably from 60 to 75 parts by weight of a thermoplastic polymer or a polymer having elastomeric properties;

b) from 3 to 20, preferably from 5 to 15 parts by weight of the aforementioned product of the reaction between cyanuric acid and piperazine; and optionally c) from 5 to 30, preferably from 10 to 20 parts by weight of one or more ammonium phosphates or an amine phosphate, or phosphoric esters.

The polymers that can be used to prepare the compositions of the present invention comprise: polymers and copolymers, or their mixtures, obtained by sequential polymerization of olefins having the formula R—CH═CH$_2$, where R is hydrogen or an alkyl radical with 1–6 carbon atoms or an aryl radical, preferably phenyl.

In particular, said polyolefins comprise:
1) isotactic or prevailingly isotactic polypropylene;
2) HDPE, LLDPE and LDPE
3) crystalline copolymers of propylene with ethylene and/or other C$_{4-10}$ linear or branched alpha-olefins, such as, 1-butene, 1-hexene, 1-octene and 4-methylpentene;

4) elastomeric ethylene/alpha-olefin copolymers and ethylene/alpha-olefins/diene terpolymers containing smaller proportions of diene e.g. 10 wt. %, preferably 5 wt. %, where the alpha-olefin is preferably selected from among propylene, 1-butene, 1-pentene, 1-hexene, 4-methyl-1-pentene and 3-methyl-1-butene (examples of dienes among those most commonly present in the above-mentioned elastomeric copolymers are butadiene, ethylidenenorbornene and 1,4-hexadiene);

5) heterophasic polymers obtained by sequential polymerization, comprising (A) a crystalline homopolymer fraction of propylene or one of the copolymers set forth in item (3), and (B) a copolymeric fraction comprising an elastomeric copolymer set forth in item (4);

6) polymers obtained from diolefins or cycloolefins, such as polyisoprene and polybutadiene, polycyclopentene, polynorbornene, copolymers or terpolymers thereof and mixtures thereof.

Other examples of commonly used polymers are polystyrene, polyamide, polyurethane (polyester and polyether), polyethylene terephthalate, and polybutylene terephthalate, and ABS and SAN copolymers.

Among the phosphates, the ammonium polyphosphates are preferred, which belong to the general formula $(NH_4)_{m+2}P_mO_{3m+1}$, in which m represents a whole number equal to or greater than 2; preferably, the molecular weight of the polyphosphates ahould be high enough to guarantee low solubility in water. Generally, m is preferably from 2 to 500.

The composition of the polyphosphates having the formula indicated above, in which m is a sufficiently large number, preferably comprised between 5 and 500, is essentially that which corresponds to the formula of the metaphosphates $(NH_4PO_3)_m$. An example of such polyphosphates is that known by the trade name "Phos-Chek P/40" (Monsanto Chemical), having the composition $(NH_4PO_3)_m$, where m is greater than 50; another example is the product known by the trademark "Exolit 422" (Hoechst), which has a similar composition.

Another polyphosphate that can be used to advantage, especially due to its reduced solubility in water, is that with the trademark "Exolit 462" (Hoechst) and corresponding to Exolit 422 polyphosphate, microencapsulated in melamineformaldehyde resin.

Other appropriate phosphates are those derived from diethylammonium phosphate, ethylenediamine phosphate, melamine ortho- or pyrophosphate.

Examples of appropriate phosphoric esters are: organic phosphites, phosphates or phosphonates, such as triphenyl phosphate, diethyl methylphosphonate, diethyl phenyl phosphonate, triphenyl phosphite, phenyl diphenylphosphonate, phenylbis(2-ethylhexyl)phosphonate, tris(2-ethylhexyl)phosphate and trinonylphenyl phosphate.

The compositions of the present invention can also contain the additives commonly used for the polymers, in particular stabilizers, such as phenolic antioxidants, phosphites, or phosphates, organic phosphonates or phosphonites; light stabilizers, such as sterically hindered amines (HALS); synergic flame retardants compound, such as the arsenic, antimony and bismuth oxides; pigments and fillers.

Formula (I) piperazine cyanurate can be prepared by reacting cyanuric acid $(C_3H_3N_3O_3)$ and piperazine $(C_4N_2H_{10})$ in an aqueous solution or a polar organic solvent, for example methanol.

From the aqueous solution of the reagents, a product precipitates which, depending on the reaction conditions, can comprise or consist of one or more compounds of formula (I). The reaction is prefarably conducted at the boiling temperature of the solution of cyanuric acid and piperazine.

The compositions of the present invention ca be prepared according to conventional methods, for example by mixing the polymer with the additives in a turbomixer at a temperature equal to or above the softening temperature of the polymer with which they are to be combined, and extruding the mixture in an extruder at the most appropriate temperature for obtaining the product in granules.

The following examples are given by way of nonlimiting illustration of the present invention.

EXAMPLES 1-2

In a 1-liter flask equipped with an agitator, a reflux refrigerator, and an outlet for vacuum, 200 ml water, an appropriate quantity of cyanuric acid $(C_3H_3N_3O_3)$ and an appropriate quantity of piperazine $(C_4N_2H_{10})$ are charged at room temperature. The solution is then brought to boiling temperature and is stirred for 2 hours to reflux.

The reaction mixture is then left to cool and the solids settle. The resulting solid product is filtered as a white powder.

The quantity of reagents used and the elementary analysis of the obtained product are reported in Table 1.

For both the products obtained (Example 1 and Example 2), the TGA (thermogravimetry) shows a clear paek between 140° C. and 150° C. equal to a weight loss of 4.90% with respect to the initial weight. Both the products obtained (Example 1 and Example 2) present a wide IR absorption band between 2000 and 3600 nm due to the O—H bond of the water.

It is thus determined from all the analytical data that the product obtained in Examples 1 and 2 is the compound of formula (I), in which n is 2 and p is 1, and having the following percent composition, by weight: C %=33.1; H %=4.9; N %=30.9; O %=30.9.

This product is then used to prepare the compositions of the present invention. Samples of such compositions are evaluated for flame-extinguishing properties.

Such samples are prepared by mixing in cold conditions Moplen FL F20 isotactic polypropylene in flake form having MFR 12 g/10 min and an isotactic index of about 96%, with appropriate quantities of the previously prepared products and of the following additives:
Exolit 422 polyphosphate,
synthetic hydrotalcite (SHT),
$TiO_2$,
Irgafos 168 tris(2,4-di-tert-butylphenyl) phosphite (Ciba-Geigy),
Irganox 1010 pentaerythrityltetrakis[3-(3,5-di-tert-butyl- 4-hydroxyphenyl)propanoate] (Ciba-Geigy).

Said mixture is then extruded in a single-screw extruder. The granules thus obtained are die-cast into plates about 1.6 mm thick, from which the samples for the flame-resistance tests are prepared.

The level of flame-resistance is determined on the samples, both by measurement of the oxygen index (according to norm ASTM 2836) and by applying norms UL 94 (published by Underwriters Laboratories, USA).

The measurement of the oxygen index expresses the minimum concentration of oxygen (expressed in % by volume) in an oxygen-nitrogen mixture, that allows the sample of the material to burn continually, after lighting a flame fed by butane gas, for 3 minutes and/or 50 mm of length of the sample.

The UL 94 test is conducted on vertically positioned samples of the indicated thickness; this consists in placing a 3-mm-high source inclined at a 45 angle in contact with one end of the sample. The switch-off time and whether or not the material drips during combustion are checked from the moment the source is removed. The material based on the measurements obtained is classified as follows:

V-0 when the mean time of flame extinction is less than or equal to 5 seconds (5 samples for 2 lightings each);

V-1 when the mean time of flame extinction is less than or equal to 25 seconds;

V-2 when it follows the V-1 behavior and drips drops of burning melted polymer which can light a cotton wad placed 5 mm below.

For each sample, three tests are carried out. The quantities and types of reagents used in preparing the compositions are reported in Table 1, along with the results of the flame-resistance tests.

Other features, advantages and embodiments of the invention disclosed herein will be readily apparent to those exercising ordinary skill after reading the foregoing disclosure.

In this regard, while specific embodiments of the invention have been described in considerable detail, variations and modifications of these embodiments can be effected without departing from the spirit and scope of the invention as described and claimed.

TABLE 1

| Preparation of piperazine cyanurate | | | |
|---|---|---|---|
| Cyanuric acid | g | 60.60 | 75.40 |
| Piperazine | g | 39.40 | 24.60 |
| Product obtained | g | 60 | 99 |
| Elementary analysis: | | | |
| C% | | 32.40 | 32.70 |
| H% | | 4.80 | 5.15 |
| N% | | 30.20 | 29.50 |
| O% | | 31.40 | 31.20 |
| Preparation of the polymer compositions | | | |
| Moplen FL F20 polypropylene | wt % | 69.2 | 69.2 |
| Exolit 422 polyphosphate | wt % | 20 | 20 |
| Piperazine cyanurate | wt % | 10 | 10 |
| SHT | wt % | 0.40 | 0.40 |
| TiO2 | wt % | 0.20 | 0.20 |
| Irganox 1010 | wt % | 0.05 | 0.05 |
| Irgafos 168 | wt % | 0.15 | 0.15 |
| Oxygen index | | 34.5 | 36.0 |

TABLE 1-continued

| UL 94 | V-O | V-O |
|---|---|---|

We claim:

1. A piperazine cyanurate having the formula:

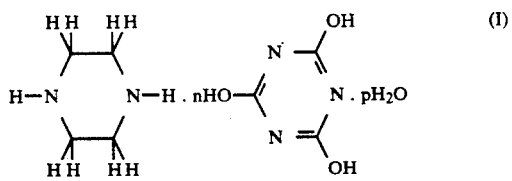

(I)

wherein n is from 1 to 2 and p is from 0 to 3.

2. The piperazine cyanurate of claim 1, wherein n is 2 and p is 1.

3. A self-extinguishing composition, comprising a thermoplastic polymer or a polymer having elastomeric properties and the product of the reaction between cyanuric acid and piperazine, said product comprising or consisting of one or more compounds of formula (I) as defined in claim 1.

4. The self-extinguishing composition of claim 3, comprising:
a) from 90 to 50 parts by weight of one or more thermoplastic polymers or polymers having elastomeric properties;
b) from 3 to 20 parts by weight of the reaction product of cyanuric acid and piperazine; and optionally
c) from 5 to 30 parts by weight of one or more ammonium polyphosphate or an amine phosphate, or of a phosphoric ester selected from the group consisting of organic phosphites, phosphates and phosphonates.

5. The self-extinguishing composition of claim 3, wherein the thermoplastic polymers or polymers having elastomeric properties are selected from the group consisting of polymers and copolymers, or mixtures thereof obtained by sequential polymerization, of olefins of the formula R—CH=CH$_2$, where R is a hydrogen atom or an alkyl radical having 1–6 carbon atoms or an aryl radical.

6. The self-extinguishing composition of claim 3, wherein the reaction product of cyanuric acid and piperazine is a piperazine cyanurate of formula

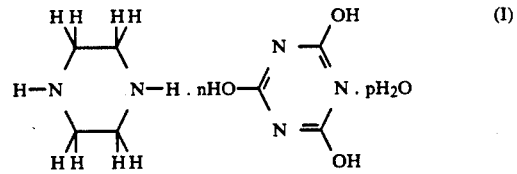

(I)

in which n is 2 and p is 1.

* * * * *

UNITED STATES PATENT AND TRADEMARK OFFICE
CERTIFICATE OF CORRECTION

PATENT NO. : 5,182,321

DATED : January 26, 1993

INVENTOR(S) : Bertelli et al

It is certified that error appears in the above-identified patent and that said Letters Patent is hereby corrected as shown below:

Col. 3, line 49, after "from" insert --amines, as for example dimethylammonium phosphate or--.

Col. 5, line 10, after "45" insert --°--.

Signed and Sealed this

Twenty-third Day of November, 1993

Attest:

BRUCE LEHMAN

Attesting Officer     Commissioner of Patents and Trademarks